(12) United States Patent
Connor

(10) Patent No.: US 9,113,776 B2
(45) Date of Patent: Aug. 25, 2015

(54) SYSTEMS AND METHODS FOR SECURE PORTABLE PATIENT MONITORING

(75) Inventor: Christopher William Connor, Arlington, MA (US)

(73) Assignee: ANAESTHESIA ASSOCIATES OF MASSACHUSETTS, P.C., Westwood, MA (US)

( * ) Notice: Subject to any disclaimer, the term of this patent is extended or adjusted under 35 U.S.C. 154(b) by 150 days.

(21) Appl. No.: 13/247,349

(22) Filed: Sep. 28, 2011

(65) Prior Publication Data

US 2012/0075060 A1    Mar. 29, 2012

Related U.S. Application Data

(60) Provisional application No. 61/387,271, filed on Sep. 28, 2010.

(51) Int. Cl.

| | |
|---|---|
| *H04W 12/06* | (2009.01) |
| *A61B 5/00* | (2006.01) |
| *G06Q 50/22* | (2012.01) |
| *H04W 88/02* | (2009.01) |
| *G06F 19/00* | (2011.01) |
| *G06F 21/42* | (2013.01) |
| *G06F 21/43* | (2013.01) |
| *G06F 21/31* | (2013.01) |
| *H04W 88/04* | (2009.01) |

(52) U.S. Cl.
CPC .............. *A61B 5/002* (2013.01); *G06F 19/327* (2013.01); *G06F 19/3418* (2013.01); *G06Q 50/22* (2013.01); *A61B 5/0006* (2013.01); *G06F 19/321* (2013.01); *G06F 19/322* (2013.01); *G06F 21/31* (2013.01); *G06F 21/42* (2013.01); *G06F 21/43* (2013.01); *H04W 12/06* (2013.01); *H04W 88/02* (2013.01); *H04W 88/021* (2013.01); *H04W 88/04* (2013.01)

(58) Field of Classification Search
CPC . G06F 21/31; G06F 21/42; G06F 2221/2129; A61B 5/0002; G06Q 50/24; A61N 1/37247; H04W 12/06; H04W 88/02; H04W 88/04; H04W 88/021
USPC ............. 128/903; 340/5.51; 600/300; 607/60
See application file for complete search history.

(56) References Cited

U.S. PATENT DOCUMENTS

| | | | | |
|---|---|---|---|---|
| 5,668,876 | A | * | 9/1997 | Falk et al. ..................... 380/271 |
| 6,057,758 | A | * | 5/2000 | Dempsey et al. ......... 340/539.12 |
| 6,398,727 | B1 | | 6/2002 | Bui et al. |
| 6,551,252 | B2 | | 4/2003 | Sackner et al. |
| 6,684,090 | B2 | | 1/2004 | Ali et al. |
| 7,002,468 | B2 | * | 2/2006 | Eveland et al. .......... 340/539.12 |
| 7,438,683 | B2 | | 10/2008 | Al-Ali et al. |
| 7,921,282 | B1 | * | 4/2011 | Mukerji et al. ............... 713/151 |
| 8,172,752 | B2 | * | 5/2012 | Russ .............................. 600/300 |
| 8,185,947 | B2 | * | 5/2012 | Kurapati et al. ................ 726/15 |
| 2006/0017579 | A1 | | 1/2006 | Albert et al. |
| 2011/0313789 | A1 | * | 12/2011 | Kamen et al. ..................... 705/3 |

* cited by examiner

*Primary Examiner* — Ariel Balaoing
*Assistant Examiner* — Benyam Haile
(74) *Attorney, Agent, or Firm* — Ropes & Gray LLP

(57) ABSTRACT

A patient monitoring system that enables a healthcare provide to request access to patient data via interaction directly with a local patient monitor and subsequently provide patient data to the healthcare provider's portable communication device regardless of device location.

11 Claims, 6 Drawing Sheets

SYSTEMS AND METHODS FOR SECURE PORTABLE PATIENT MONITORING

CROSS-REFERENCE TO RELATED APPLICATIONS

This application claims the benefit of U.S. Provisional Application 61/387,271 filed on Sep. 28, 2010, the entirety of which is incorporated herein by reference.

BACKGROUND

Patient monitoring systems are widely used in the medical field to enable healthcare providers to monitor the condition of patients. Patient monitoring systems enable healthcare providers to remotely monitor patients from a central monitoring station, e.g., a nurses' station, that is in communication with multiple local patient monitors. Local patient monitors, e.g., oximeters, ECGs, or pulse rate monitors, are typically connected to a central station via a wired or wireless network in a healthcare facility. The central station may store patient data or interface with medical record databases as part of an electronic medical record (EMR) system.

Wired communications between a local patient monitor and central station is typically via a local area network using an Ethernet protocol. Wireless communications between a local patient monitor and central station is typically via a wireless local area network using a wireless Ethernet protocol based on the 802.11 family of standards. Some local monitors utilize a personal area network such as Bluetooth to support wireless communications with one or more patient sensors or to communication with a central station via an access point.

Communications between a local patient monitor and a central station or between a local patient monitor and a sensor may be protected by encryption of the data being communicated. Some patient monitoring systems support remote monitoring of patient physiological parameters via pagers, personal digital assistants (pda), and other portable computing devices that communicate with a central station or local patient monitor via the Internet or a wireless access point on the premises of a healthcare facility.

Unfortunately, existing patient monitoring systems, including local patient monitors, do not provide an efficient way of allowing a healthcare provider, e.g, physician, to securely access monitored patient physiological parameters using a portable communications device. Accordingly, there is a need to enhance the ability of healthcare providers to more efficiently and securely obtain access to local patient physiological data using a portable computing or communications device.

SUMMARY

The application, in various embodiments, addresses the deficiencies of current patient monitoring and management systems by providing systems and methods that enable a healthcare provider to efficiently establish an authenticated and secure communications link between a patient monitoring system and a portable communications device.

The systems and methods described herein refer to a portable (e.g., handheld) communications device such as, for example, a smart phone or personal digital assistant (pda) that a healthcare provider can use to access patient physiological data gathered by one or more patient monitors. In a hospital setting, multiple patients occupy multiple separate rooms dispersed throughout a hospital floor, or across multiple hospital floors, or across multiple hospital buildings. For example, patients may be dispersed across a suite of operating rooms or across different anesthetizing locations. A central monitoring station or nurses' station is usually connected via a data network to patient bedside monitors in the multiple patient rooms or locations so that patient physiological data associated with each of the multiple patients can be monitored conveniently at the central station. For example, when patients are dispersed across various anesthetizing locations, a clinician may wish to monitor a patient in the Interventional Radiology department while also monitoring patients in operating suits and other rooms.

Healthcare personal often make rounds where they visit the bedside of each of the patients to observe each patient's physical conditions and observe the bedside monitors for each patient. The present application enables a healthcare provide, in close proximity to a local and/or bedside patient monitor, to use a portable communications device to request and obtain access to patient data being gathered by a particular patient monitoring device or group of patient monitoring device.

Unlike existing patient monitoring systems, the systems and methods describes herein enable a healthcare provider to advantageously and conveniently obtain access to patient data using an local wireless or wired connection directly with a particular patient monitor. By requiring the healthcare provider, e.g., a physician, and/or their portable communications device to be physically present and in close proximity to a patient monitor or monitoring device, the system ensures that only a healthcare provider with physical access to a particular patient can have electronic access to their physiological data. Thus, a healthcare provider may be required to go to the patient and their bedside monitor to obtain access to the patient's data using a portable communications device. The local wireless connection and/or channel used to request access to patient data will preferably be a different (out-of-band) than the wireless connection and/or channel used by the patient monitoring device to send patient data to a remote display station such as a central monitoring station. The out-of-band wireless channel may include a personal area network (PAN) protocol such as, without limitation, Bluetooth or an 802.11-based wireless channel. The wireless channel used by the patient monitoring device to send data to the central station may include a Bluetooth, 802.11 or other wireless standards.

When requesting access to patient data via a local patient monitor, the portable communications device may provide an access code to the patient monitoring device. The access code may include a passcode, password, an encrypted value, and/or a cryptographic response. The patient monitoring device may use the access code to determine whether the healthcare provider and/or portable communications device should be allowed access to monitored patient data. The wireless channel and/or any portion of communications between the system, local monitor, and/or portable communications device may be encrypted to provide data privacy. The system may use secret keys and/or ephemeral secret keys that can be changed based on certain conditions and/or events.

Once a portable communications device and/or healthcare provider is authorized by a monitor with access to patient data, the portable communications device may continuously receive real-time or near real-time patient data. The portable monitoring device may use a further interface and wireless channel to receive the patient data and then display the data via a user interface such as a graphical user interface. The wireless channel used by the portable communications device to receive patient data may include a wireless channel other than the wireless channel used to communicate with the local patient monitoring device. For example, if the portable communications device is a 3GSM capable smart phone, the device may communicate with its mobile 3GSM provider to obtain a steam of the patient data via a 3GSM wireless data channel. Communications with the local monitor to obtain patient data access, on the other hand, may be via a Bluetooth connection. Thus, once access to patient data is established, the healthcare provider is free to move to any location, even far away from the patient monitoring device, while still receiving the patient data using their portable communications device via the 3GSM connection.

BRIEF DESCRIPTION OF THE DRAWINGS

The foregoing and other objects and advantages of the invention will be appreciated more fully from the following further description thereof, with reference to the accompanying drawings. The skilled person in the art will understand that the drawings, described below, are for illustration purposes only. The drawings are not intended to limit the scope of the applicant's teaching in any way.

DETAILED DESCRIPTION

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

Figure 1:
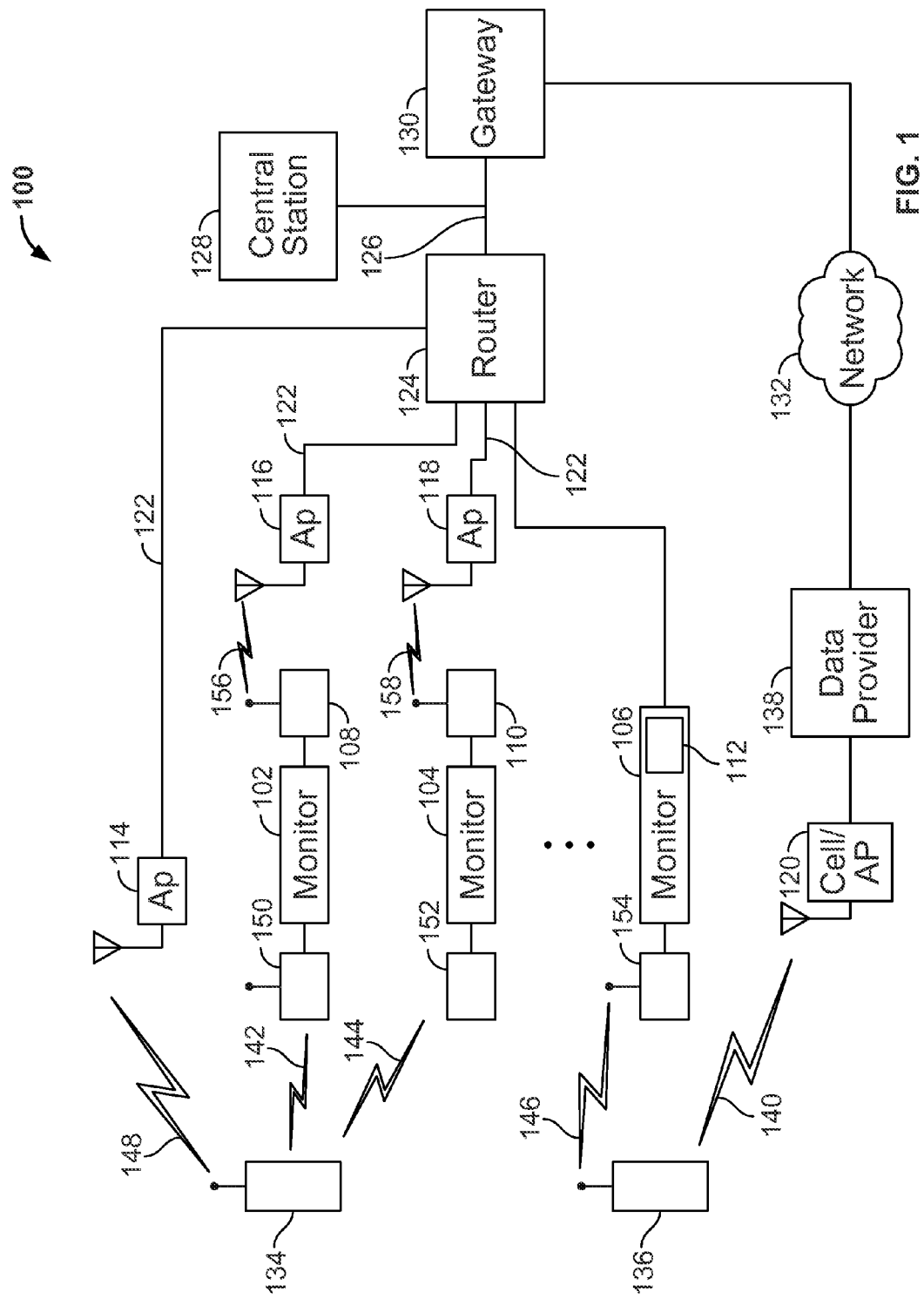
FIG. 1 shows the general architecture of a patient monitoring system 100 according to illustrative aspect of the invention.

FIG. 1 shows the general architecture of a patient monitoring system 100 according to an illustrative aspect of the invention. The system 100 includes a number of patient monitors 102, 104, and 106 that monitor physiological parameters of one or more patients in one or more rooms or locations within a healthcare facility. Each of the patient monitors 102 and 104 is connected to a wireless remote telemeters 108 and 110, respectively, that collect, packetize and transmit the physiologic data of patients. (As used herein, the term "wireless" means data is transferred to and/or from the device over a wireless medium.) The remote telemeters 108 and 110 may include patient-worn (ambulatory) remote telemeters which connect directly to a patient or instrument remote telemeters that connect to a bedside or other local patient monitors 102, 104, and 106. The patient monitor 106 may include an integrated or internal transceiver 112 or network interface card (NIC) capable of exchanging data via a wired communications medium, e.g., an Ethernet cable. The physiologic data transmitted by the remote telemeters and/or transceiver 108, 110, and 112 may include, for example, real-time ECG signals, blood pressure readings, $CO_2$ levels, and temperature readings. The remote telemeters 106, 108, and 110 may additionally sense and transmit various types of non-physiologic data, such as battery-level status data, ECG loose-lead status data, and patient location data. (The term "patient data" may refer collectively to the physiologic and non-physiologic data captured by the remote telemeters 106, 108, and 110.)

The remote telemeters 108 and 110 may communicate bi-directionally with any number of radio transceivers 114, 116, 118, and 120, referred to as access points (AP). The APs may use one of various types of wireless protocols and standards such as time division multiple access (TDMA), code division multiple access (CDMA), 802.11, Wifi, Bluetooth, cellular, GPRS, LTE, EVDO, WiMax, and the like. In one mode of operation, each AP can communicate with multiple remote telemeters at-a-time. The APs may be spaced apart from one another throughout the hospital or healthcare facility to provide a "cell-like" coverage area which consists of overlapping zones of coverage.

Different APs 114-120 of the system 100 may operate (i.e., transmit and receive data) on a different RF frequency channels ("frequencies"). However, APs that are sufficiently spaced apart to avoid interference with one another may operate on like frequencies. Although the remote telemeters 108 and 110 and APs shown in FIG. 1 are of the type which communicate by radio frequency (RF), the system may also include "hardwired" remote telemeters 112 and APs which communicate over hardwire connections.

With further reference to FIG. 1, the APs 114-118 are connected by conventional shielded twisted pair lines 122 to a router 124. The router 124 may alternatively or additionally function as a switch, relay, server, gateway, repeater, bridge, and/or like network communications device. In one configuration, the router 124 can accommodate up to sixteen APs. In other configurations, the router 124 can accommodate greater than sixteen APs. In a typical hospital installation, one router 124 may service a single floor of a hospital. The router 124 may provide connectivity between the APs on a hospital local area network (LAN) 126. The LAN 126 may serve as a real-time data distribution system for distributing the physiologic data of the patients with a known latency. The LAN 126 may includes a 100 Mbit/second backbone which is based on the 100BaseTx (Ethernet) protocol. (The term "backbone" may refer generally to the transmission medium and the networking cards of the LAN.) Alternative LAN protocols which could be used include ATM (Asynchronous Transfer Mode) and FDDI (Fiber Distributed Data Interface) and others.

The LAN 126 may include one or more central stations 128 or charting servers for allowing hospital personnel to remotely view and otherwise monitor the real-time physiologic data of the patients of the system 100. Each monitoring station 128 is preferably in the form of a standard PC (personal computer) which runs conventional patient monitoring software. The LAN 126 may also include one or more gateway computers 130 for connecting the LAN 126 to other networks 132, such as the Internet, to permit the exchange of patient information with other medical facilities and patient sites.

As will be apparent, the architecture illustrated in FIG. 1 provides for a high degree of scalability. The system 100 can initially be installed with central station 128 serving as the sole monitoring station for a set of 16 (or fewer) APs, which may include both RF and hardwired connections. With the addition of a LAN 126, new APs and routers 124 can be added to increase the patient capacity and/or coverage area of the system 100. The architecture allows new APs to be added to the system 100 without a corresponding degradation in performance caused by noise. Monitoring or central stations 128 can be added to the LAN 126 as needed to permit the remote viewing and monitoring of patient data from various locations within the hospital or healthcare facility.

The system 100 also includes portable communications devices 134 and 136. The portable communications devices 134 and 136 may include a pda, portable computer, cellular telephone, smart phone, wireless communications device, and the like. The devices 134 and 136 may utilize one or more communications protocols such as 802.11, WiMax, Wifi, GPRS, CDMA, LTE, pager protocols, Bluetooth, a PAN protocol, a wireless LAN protocol, a wide area network (WAN) protocol, or any suitable wireless protocol to enable communications with one or more monitors 102, 104, and 106; APs 114 116, 118, 120; or with a data provider 138. The data provider 138 may include a public land mobile network (PLMN) or other wireless data provider. The AP 120 may include a cellular network base station and antenna to facilitate mobile network communications with the devices 134 and 136 via a wireless channel 140. The device 134 may communicate with the LAN 126 via a wireless channel 148 and AP 144.

The devices 134 and 136 may communicate with the patient monitors 102, 104, and 106 via channels 142, 144, and 146 respectively. Channels 142, 144 and 146 may include wireless channels and/or wired channels. Each patient monitor 102, 104, and 106 may include a transceiver 150, 152, and 154 to enable the exchange of data between the devices 134 and 136 and the monitors 102, 104, and 106. In some instances, the functions of, for example, transceivers 150 and 108 are combined into a single transceiver element. In some instances, the transceivers 108, 110, 150, 152, and 154 are integrated with the monitors 102, 104, and 106 respectively.

In operation, the telemeters 108, 110, and 112 send data packets to individual APs 116 and 118 using a wireless protocol, and to router 124 using a wired protocol. These packets include the patient data collected by the remote telemeters (or by patient monitors 102, 104, and 106 connected to the remote telemeters), along with the ID codes of the respective telemeters and/or monitors. The APs 116 and 118, and NIC 112 forward these data packets to the corresponding router 124, which in-turn broadcast the patient data on the LAN 126 (in real time) for viewing and automated monitoring by the central station 128. The system may also support a patient location methods for monitoring the remote location of each patient and/or device 134 and 136.

To support patient mobility, the APs 116 and 118 and remote telemeters 108 and 110 may implement a "switchover" protocol in which the telemeters 108 and 110 continuously attempt to establish connections with those APs that offer the best link performance. As part of this protocol, each remote telemeter continuously assesses the quality of the RF link to each AP that is within range. The telemeters 108 and 110 store this link assessment information, and periodically evaluate this information to determine whether a switch-over to a new AP is desirable. When a remote telemeter 108 determines that an AP is available (i.e., has an open wireless channel) which offers better link performance than a current AP (i.e., an AP to which the telemeter is currently connected), the remote telemeter attempts to connect to the new AP. (As described below, this involves sending a request message to the selected AP 118, and then waiting for confirmation message from the AP). If the connection is successfully established, the remote telemeter 108 drops its connection to the current AP 116. Thus, a remote telemeter 108 will normally connect to many different APs (including APs of different networks or routers) as the patient moves throughout the hospital or healthcare facility. Transitions between APs occur without interruption or loss of data, and may thus be seamless from the viewpoint of the monitoring clinician. Thus, even if a previously secured communication link is lost, then the handheld device 134 will be able to re-establish a secure connection automatically.

To provide protection against dropouts caused by multi-path interference (and other types of interference), each remote telemeter 108 may attempts to maintain a connection with two APs 116 and 118 at all times. (In other implementations, the remote telemeters 108 and 110 may connect to three or more APs 114, 116, and 118 to provide even greater protection against multi-path interference.) Whenever two AP connections are established, the remote telemeter 108 may transmit each of its data packets to both of the APs. These redundant transfers take place on different wireless channels. Thus, each wireless data channel or path benefits from the protection offered by space, time, code and/or frequency diversity. Upon receiving the redundant packets, the router 124 to which the two APs are connected (assuming the APs are connected to the same router) may use error detection codes contained within the packets to discard bad packets, and to discard duplicate packets when both packets are successfully received.

In one implementation of the system 100, the remote telemeters 108 and 110 may only connect to the APs 116 and 118 of one router 124 at-a-time. In this implementation, each remote telemeter 108 and 110 attempts to stay connected to the APs of the current LAN 126, and switches over to a different router and/or LAN only when deemed necessary. In another implementation, the APs of the system are maintained sufficiently synchronized with one another to allow each remote telemeter to connect to APs of two different routers or LANs. When this situation occurs, the task of discarding duplicate packets may automatically shift to the monitoring station 128.

In certain implementations, a healthcare provider, e.g., a physician, has a portable communications device 134 in their possession as they make rounds through a healthcare facility. The healthcare provider uses the device 134 to obtain access to certain patient physiological data by interfacing, for example, with a bedside patient monitor 102 via a wireless channel 142 and transceiver 150. The wireless channel 142 may be a separate, out-of-band, channel with respect to the wireless channel 156 used by the monitor 102 and telemeter 108 to transfer physiological data to the central station 128. Thus, the provider, via the device 134, can request access to the monitored physiological data using the out-of-band wireless channel 142. In certain embodiments, at least a portion of the out-of-band channel includes a physical wired connection between the device 134 and monitor 102. In such embodiments, the monitor 102 may be physically wired to a docking station and the device 134 is placed, temporarily, in the docking station. When docked, the device 134 may download and synchronize physiological data using an out-of-band channel.

The wireless channel 142 may use the same or different protocol as the protocol used via wireless channels 156 and 158. For example, the telemeter 108 may use 802.11 to communicate via channel 156 to AP 116, while the device 134 uses Bluetooth to communicate via channel 142 with monitor 102. In some configurations, the power and/or range of the wireless channels 142, 144, and 146 may be limited to ensure that the devices 134 and 136 must be in relatively close proximity with the monitors 102, 104 and 106 to enable communications. This ensures, for example, that the device 134, and hence its user, is physically present near the monitor 102 and/or patient's bedside when requesting access to the patient's physiological data via the device 134. The device 134 may also be physically connected to the monitor temporarily to facilitate and access request.

Once an access request is made by the device 134 and accepted by the monitor and/or system 100 (to be discussed in more detail below), the device 134 may receive physiological data originating from, for example, monitor 102 or central station 128 related to a patient being monitored by the monitor 102. The device 134 may receive the physiological data via the wireless channel 142. However, as the device 134 moves away from the monitor 102, the channel 142 may be lost. Thus, the device 134 may receive the patient physiological data via another wireless channel such as channel 148 and/or 140. For example, if the device 134 has 802.11 and 3GSM data capabilities, the device 134 may initially receive the physiological data via an 802.11-based channel 148 and AP 114. If or when 802.11 APs are out of range, the device 134 may switch to a mobile network using 3GSM data to receive data via, for example, cellular AP 120 and data provider 138 that enable the device 138 to access the central station 128 and/or monitor 102 via the network 132, gateway 130, and LAN 126.

Thus, once access for a healthcare provider device 134 or 136 is authorized and established locally with a patient monitor, the device 134 or 136 may be used to continuously monitor the patient data regardless of the subsequent location of the device 134 or 136 via other wireless data channels than the channel 142 or 146 uses to obtain authorization.

Each patient monitor 102, 104, and 106, central station 106, and/or a charting server may include data used to allow or authorize devices 134 and 136 access to patient data associated with one or more of the patient monitors 102-106. For example, a patient monitor 102 and/or central station 128 may include a list or database of device 134 and 136 identifiers (IDs), healthcare provider/device user IDs, monitor IDs, AP IDs, location data for APs, location data for devices 134 and/or 136, user names, digital certificates, secret keys, access codes, and the like. Each monitor and/or central station may maintain a list of groups of monitors where a set of monitors is assigned based on location (e.g., a floor), type of care (e.g., critical care unit), healthcare provider (e.g., patient of particular healthcare provider). Thus, when a device 134 is authorized access to a monitor 102, the central station 128 (charting server) and/or monitor 102 may authorize the device to access all patient data associated with a group of monitors (where the monitor 102 is part of the group). Each device 134 may include a various software applications and/or functions that enable to the device 134 to interface with the system 100.

Figure 2:
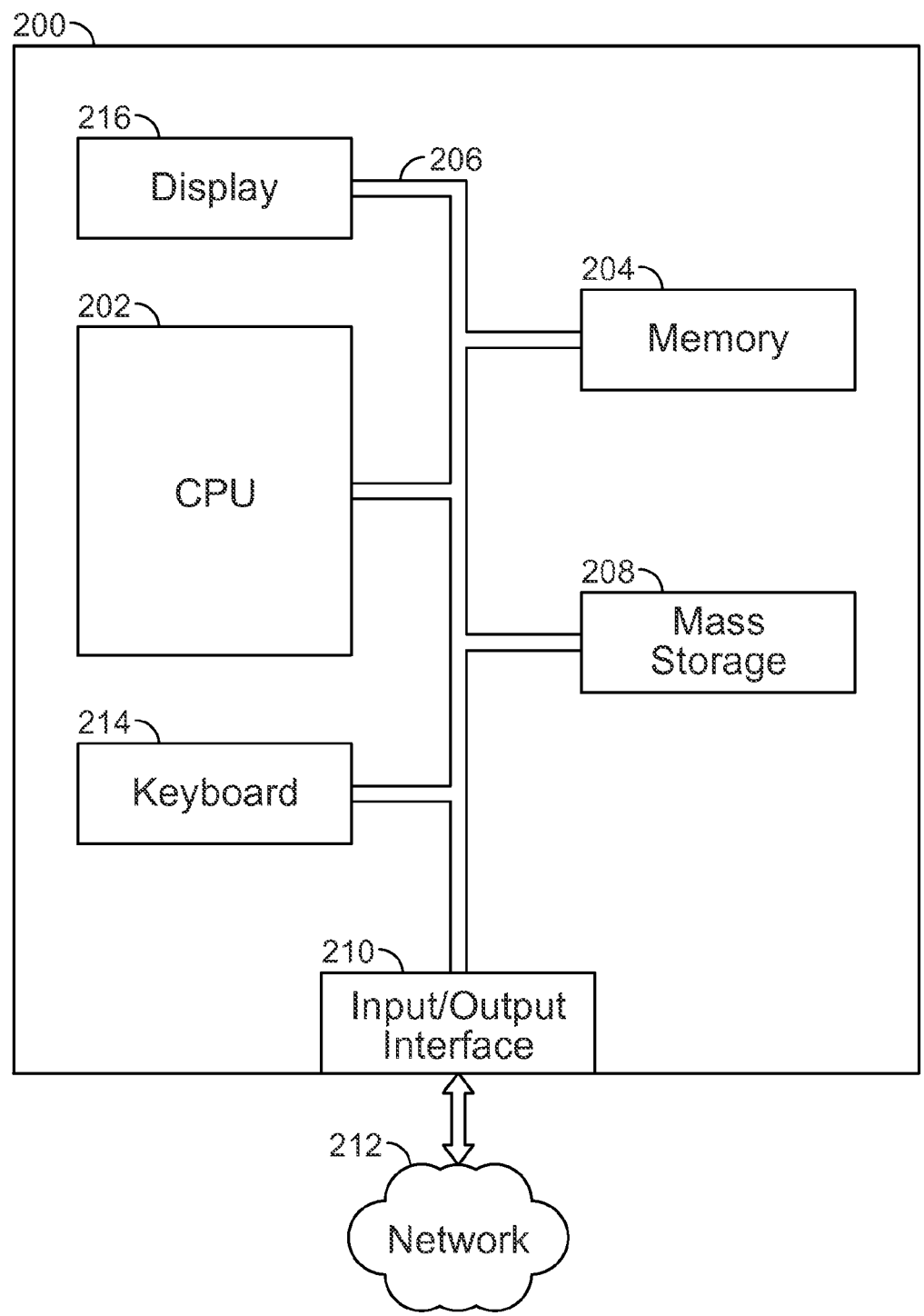
FIG. 2 includes a functional block diagram of a device, monitor, central station, or other component shown in FIG. 1 according to an illustrative embodiment of the invention.

FIG. 2 includes a functional block diagram of a general purpose computer system, e.g., portable communications device 134 or central station 128 of FIG. 1, according to an illustrative embodiment of the invention. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives or solid state memories or memory sticks, for storing data and instructions for use by the CPU 202. At least one component of the mass storage system 208, preferably in the form of a disk drive or tape drive, stores the database used for processing data and/or patient physiological data of the system 100. The mass storage system 208 may also include one or more drives for various portable media, such as a floppy disk, a compact disc read only memory (CD-ROM), or an integrated circuit nonvolatile memory adapter (i.e. PC-MCIA adapter) to input and output data and code to and from the computer system 200. The storage system 208 may store patient related physiological data for multiple patients over a period of time to enable the system 200 (or central station 128) to analyze the patient data, generate metadata or trend data and charts, and/or to present selected portions of data to users or distribute selected portions of data to devices 134 and 136.

The computer system 200 may also include one or more input/output interfaces for communications, shown by way of example, as interface 210 for data communications via the network 212 (or network 114). The data interface 210 may be a modem, an Ethernet card or any other suitable data communications device. To provide the functions of a computer 102 according to FIG. 1, the data interface 210 may provide a relatively high-speed link to a network 212 (or network 114 of FIG. 1), such as an intranet, internet, or the Internet, either directly or through an another external interface 116. The communication link to the network 212 may be, for example, optical, wired, or wireless (e.g., via satellite or cellular network). Alternatively, the computer system 200 may include a mainframe or other type of host computer system capable of Web-based communications via the network 212. The computer system 200 may include software for operating an network application such as a web server and/or web client.

The computer system 200 also includes suitable input/output ports or use the interconnect bus 206 for interconnection with a local display 216 and keyboard 214 or the like serving as a local user interface for programming and/or data retrieval purposes. The display 216 may include a touch screen capability to enable users to interface with the system 200 by touching portions of the surface of the display 216. The display 216 may enable a graphical display on one or more patient physiological parameters associated with one or more patients and/or patient monitors. Server operations personnel may interact with the system 200 for controlling and/or programming the system from remote terminal devices via the network 212.

The computer system 200 may run a variety of application programs and store associated data in a database of mass storage system 208. One or more such applications may enable the receipt and delivery of messages to enable operation as a server, for implementing server functions relating to patient management, distribution of patient physiological data, and/or information of FIG. 1.

The components contained in the computer system 200 are those typically found in general purpose computer systems used as servers, workstations, personal computers, network terminals, and the like. In fact, these components are intended to represent a broad category of such computer components that are well known in the art.

As discussed above, the general purpose computer system 200 may include one or more applications that provide patient management and information collection and distribution in accordance with features of the invention. The system 200 may include software and/or hardware that implements a web server application. The web server application may include software such as HTML, XML, WML, SGML, PHP (Hypertext Preprocessor), CGI, and like languages.

The foregoing features may be realized as a software component operating in the system 200 where the system 200 is Unix workstation or other type of workstation. Other operation systems may be employed such as, without limitation, Windows, MAC OS, and LINUX. In some embodiments, the monitor, central station, or device software can optionally be implemented as a C language computer program, or a computer program written in any high level language including, without limitation, C++, Fortran, Java, or Visual BASIC. Certain script-based programs may be employed such as XML, WML, PHP, and so on. Additionally, general techniques for high level programming are known, and set forth in, for example, Stephen G. Kochan, Programming in C, Hayden Publishing (1983). The system 200 may use a DSP for which programming principles are well known in the art.

As stated previously, the mass storage 208 may include a database. The database may be any suitable database system, including the commercially available Microsoft Access database, and can be a local or distributed database system. The design and development of suitable database systems are described in McGovern et al., A Guide To Sybase and SQL Server, Addison-Wesley (1993). The database can be supported by any suitable persistent data memory, such as a hard disk drive, RAID system, tape drive system, floppy diskette, or any other suitable system. The system 200 may include a database that is integrated with the system 200, however, it will be understood by those of ordinary skill in the art that in other implementations the database and mass storage 208 can be an external element.

In certain embodiments, the system 200 may include an Internet browser program and/or be configured operate as a web server. In some embodiments, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), for example. However, new protocols and revisions of existing protocols may be frequently introduced. Thus, in order to support a new or revised protocol, a new revision of the server and/or client application may be continuously developed and released.

In one implementation, the system 100 includes a networked-based, e.g., Internet-based, application that may be configured and run on a device 134 and/or any combination of the other components of the system 100. The system 100 (or central station 128 or monitor 102) may include a web server running a Web 2.0 application or the like. The devices 134 and 136 may include web clients. Web applications running on the system 100 may use server-side dynamic content generation mechanisms such, without limitation, Java servlets, CGI, PHP, or ASP. In certain embodiments, mashed content may be generated by a web browser via, for example, client-side scripting including, without limitation, JavaScript and/or applets.

In certain embodiments, the controller 102 may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The devices 134 and 136, monitors 102-106, and/or central station 128 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, AES, RSA, and any like public key or private key based schemes.

FIGS. 3-6 include illustrative process diagrams of various access authorization processes that may be utilized by devices 134 and 136 to obtain access to patient physiological data.

Figure 3:
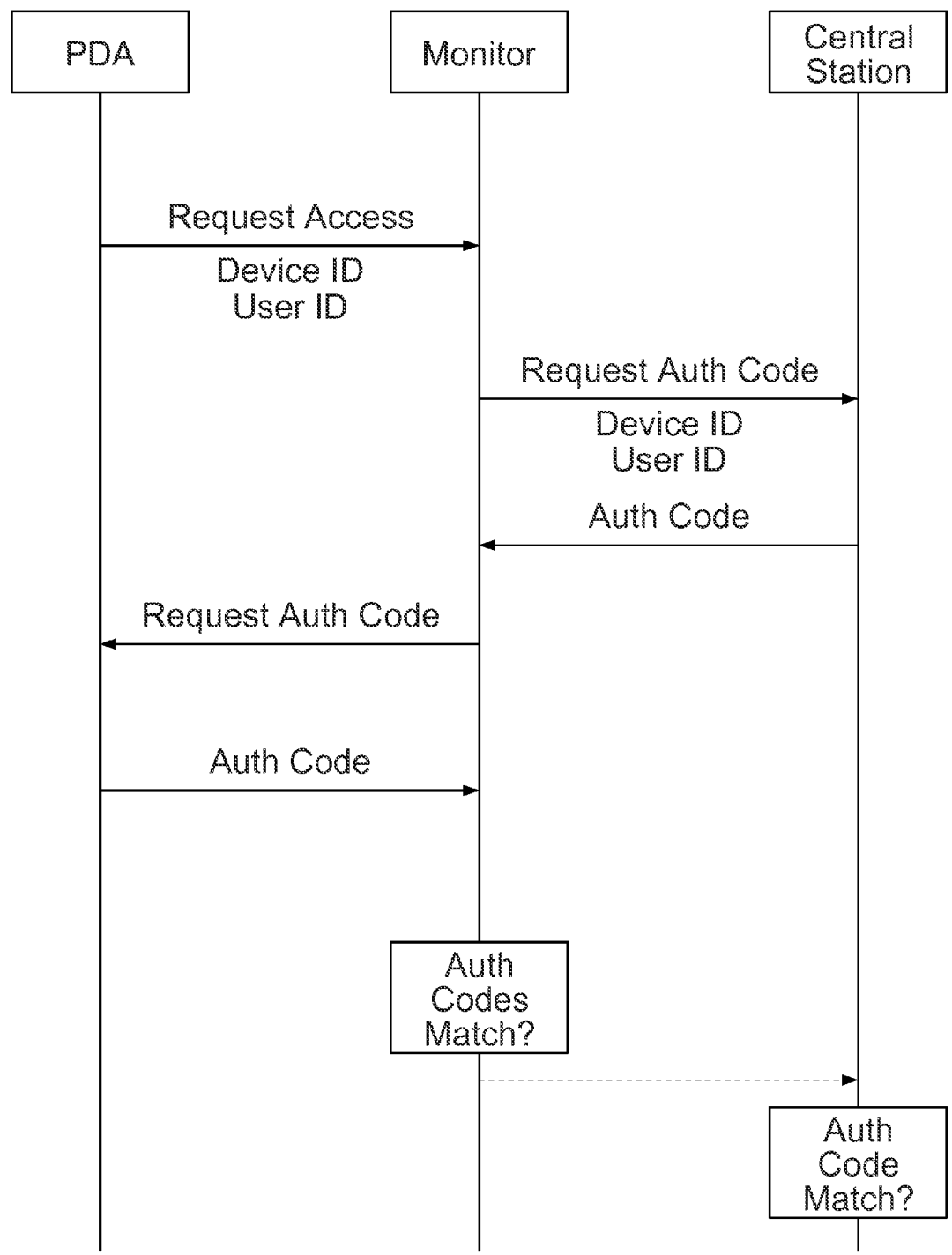
FIG. 3 shows an exemplary sequence of messages used to enable a pda, e.g., device 134, to access patient data associated with a monitor, e.g., patient monitor 102.

FIG. 3 shows an exemplary sequence of messages used to enable a pda, e.g., device 134, to access patient data associated with a monitor, e.g., patient monitor 102. First, the device 134 sends a request to the monitor 102 for access to patient data being monitored by the monitor 102. This may occur when a physician enters a patient's room in a hospital and decides to configure his device 134 (e.g., pda) to display the monitored data via the device 134. The request may include identifier information such as a device 134 ID, the user ID (physician), physician's name, room number, patient name, patient ID, and the like. The request may include additional data such as, without limitation, an IP address, port number, or session ID associated with the device 134, the monitor 102, the central station 128, and/or another network element in communication with the device 134. The monitor 102 may then forward the request to the central station 128. The central station 128 may store a list of authorization codes (e.g., magic codes) where each code may be associated with a particular device 134 or user. Using the device or user ID provided in the request, the central station 128 can access the authorization code and send it to the monitor 102.

The monitor 102 may then prompt the device 134 with a request for the authorization code which may be displayed on a display of the device 134. The user may then enter the authorization code and send it to the monitor via the wireless channel 142 which is a different, and out-of-band, channel than the wireless channel 156 used to send data to the central station 128. The monitor 102 may then compare the authorization code from the device 134 with the code from the central station 128. If the codes match, the monitor authorizes the device 134 with access to patient monitored data. Alternatively, the monitor 102 may store the authorization codes and, therefore interaction with the central station 128 is not required. As another alternative, the authorization code from the device 134 may be sent to the central station 128 which performs the comparison of codes and authorization of the device 134. Once the device and/or user is authorized access, an encrypted session and/or channel may be established between the device 134 and monitor 102 (and/or central station 128) to protect data transmissions to and from the device 134.

Figure 4:
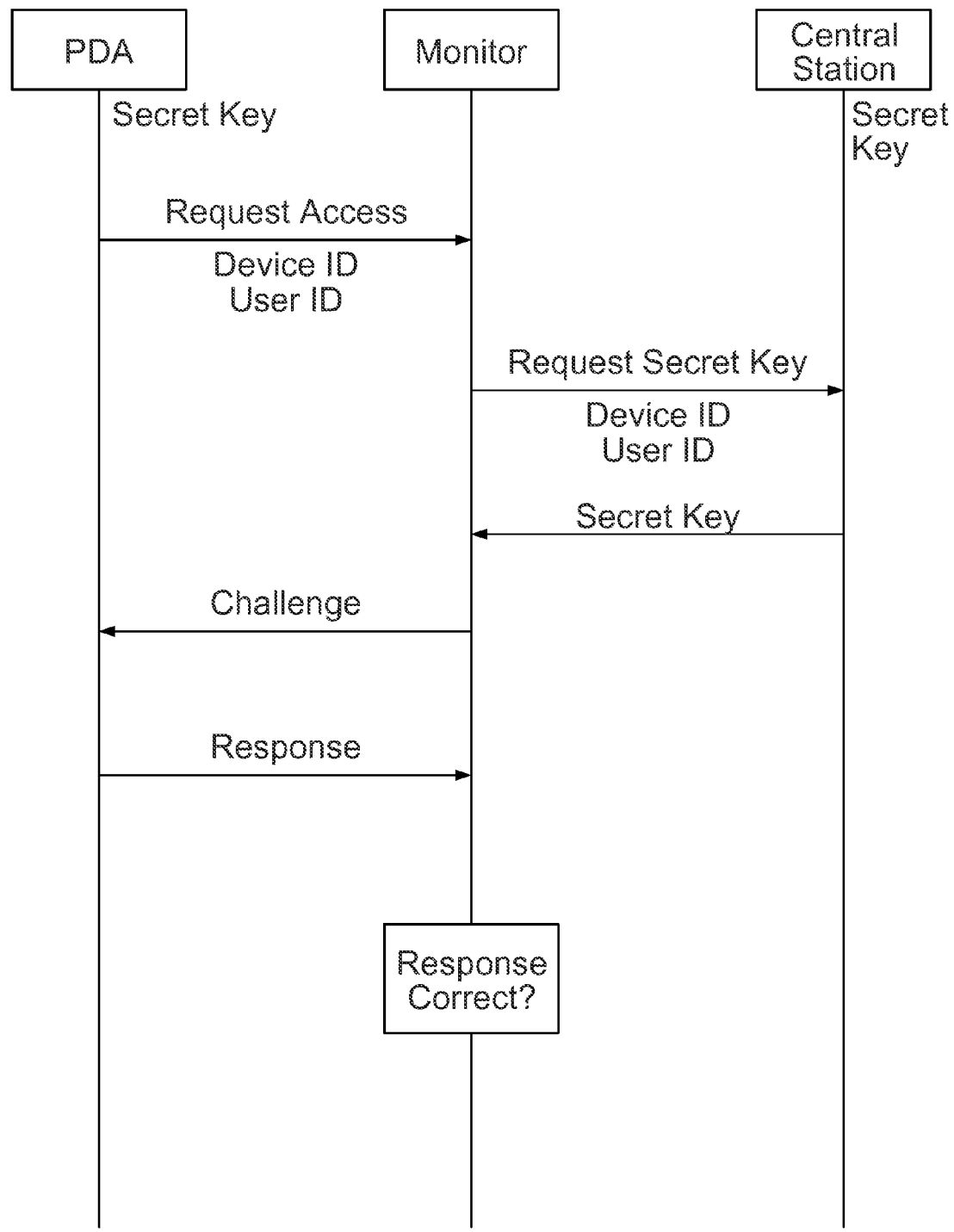
FIG. 4 shows an exemplary sequence of messages used to enable a pda, e.g., device 134, to access patient data associated with a monitor, e.g., patient monitor 102 using a cryptographic secret key and challenge-response algorithm.

FIG. 4 shows an exemplary sequence of messages used to enable a pda, e.g., device 134, to access patient data associated with a monitor, e.g., patient monitor 102 using a cryptographic secret key and challenge-response algorithm. The process is similar to that in FIG. 3, except that the device 134 and central station 128 (or monitor 102) share the same secret key. The secret key is used by the device 134 to generate a response to a challenge from the monitor 102. Because only the device 134 knows the particular secret key, only the device 134 can generate the correct response. The monitor 102 using the secret key generates its own version of the response and then compares the device 134 response to its response. If the responses match, the monitor 102 authorizes access to its patient data to the device 134. Again, the authorization/authentication functions of the monitor 102 may be performed by the central station 128 instead or performed solely by the monitor 102. Once the device and/or user is authorized access, an encrypted session and/or channel may be established between the device 134 and monitor 102 (and/or central station 128) to protect data transmissions to and from the device 134.

Figure 5:
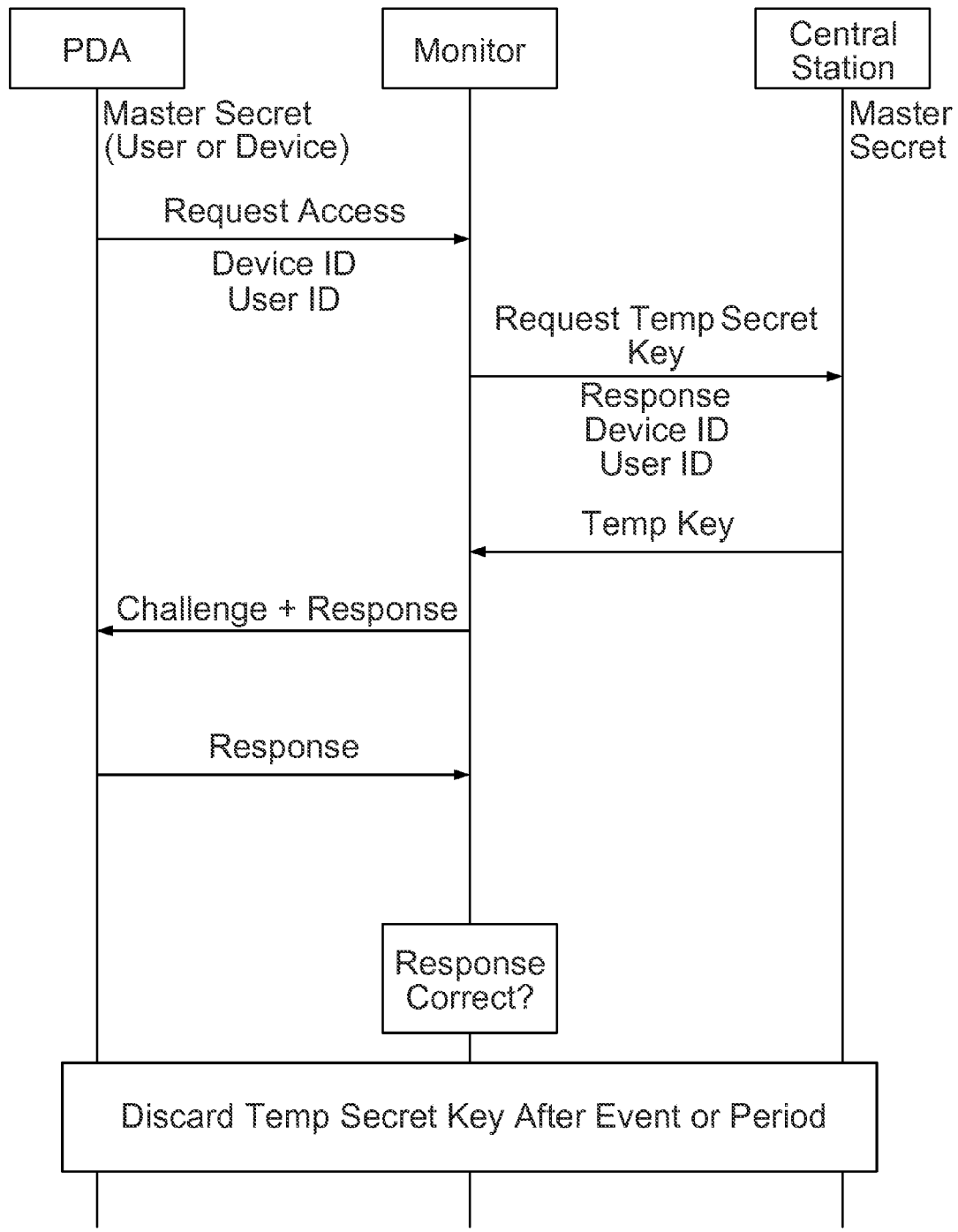
FIG. 5 shows an exemplary sequence of messages used to enable a pda, e.g., device 134, to access patient data associated with a monitor, e.g., patient monitor 102 using a ephemeral or temporary secret key and challenge-response algorithm.

FIG. 5 shows an exemplary sequence of messages used to enable a pda, e.g., device 134, to access patient data associated with a monitor, e.g., patient monitor 102 using a ephemeral or temporary secret key and challenge-response algorithm. The process is similar to that in FIG. 4, except that the device 134 and central station 128 (or monitor 102) generate the same ephemeral secret key. The ephemeral key is generated based on a master secret known by device 134 and monitor 102 (and/or central station 128). The ephemeral secret key is then used by the device 134 to generate a response to a challenge from the monitor 102. Because only the device 134 knows the particular secret key, only the device 134 can generate the correct response. The monitor 102 using the secret key generates its own version of the response and then compares the device 134 response to its response. The ephemeral key may be used only once, for a period of time, or for a number of access requests, or until the occurrence of a clinical event after which it is advantageous to expire the ephemeral key. If the responses match, the monitor 102 authorizes access to its patient data to the device 134. In certain embodiments, the monitor 102 or central station 128 generates an ephemeral key. The ephemeral key may be based at least on a master secret shared by the monitor 102 and the central station 128. In such embodiments, this ephemeral key may be transmitted to the device 134 over the out-of-band channel 142. This locally-obtained knowledge of the ephemeral key may then be used to credential and secure transmission over the wide-area wireless network 148 by challenge and response. Such a technique may be advantageous because the device 134 only knows the ephemeral secret key. Thus, if the device 134 is misplaced, security is automatically regained as soon as the ephemeral secret key expires. Again, the authorization/authentication functions of the monitor 102 may be performed by the central station 128 instead or performed solely by the monitor 102. Once the device and/or user is authorized access, an encrypted session and/or channel may be established between the device 134 and monitor 102 (and/or central station 128) to protect data transmissions to and from the device 134.

Figure 6:
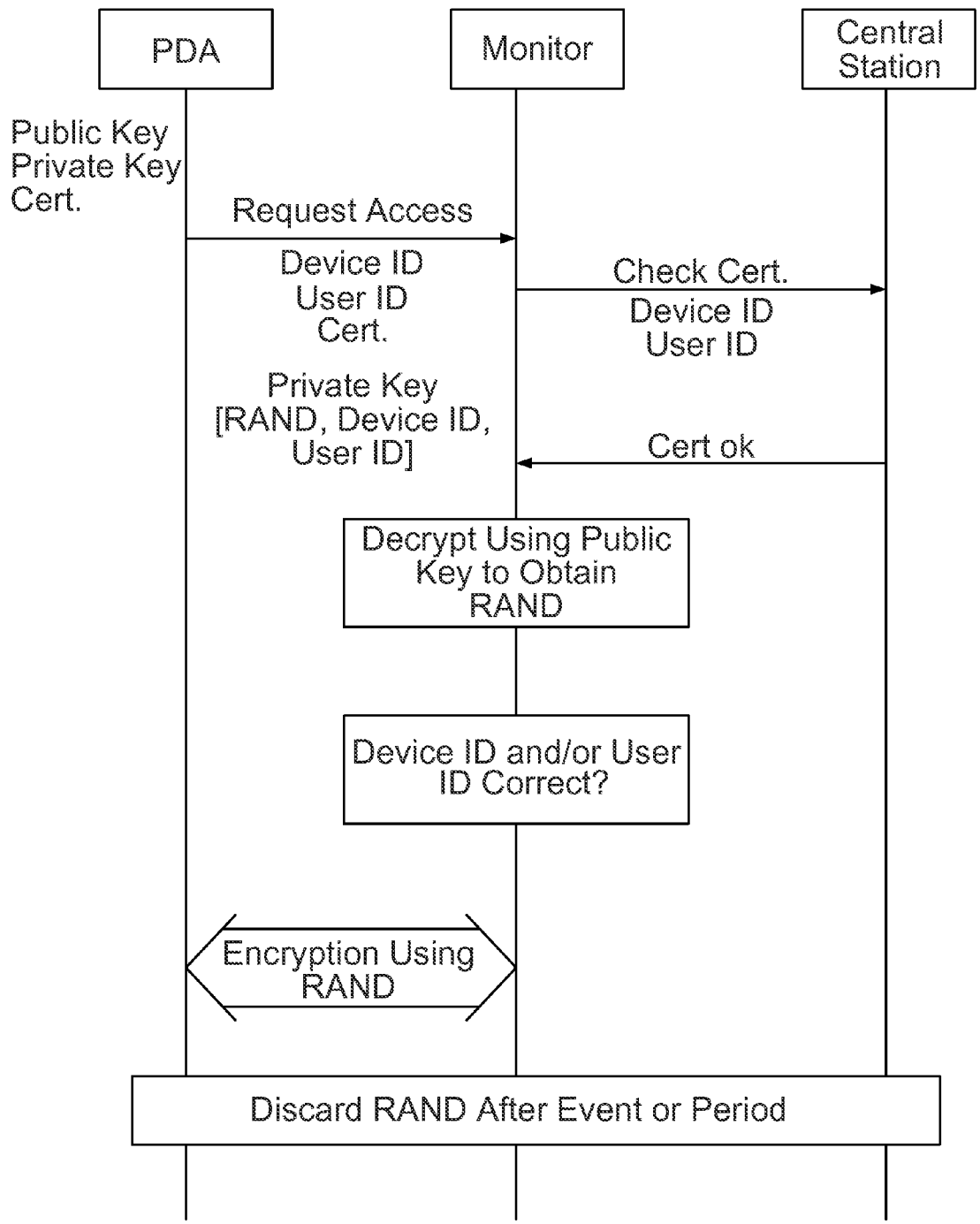
FIG. 6 shows an exemplary sequence of messages used to enable a pda, e.g., device 134, to access patient data associated with a monitor, e.g., patient monitor 102 using public key cryptography.

FIG. 6 shows an exemplary sequence of messages used to enable a pda, e.g., device 134, to access patient data associated with a monitor, e.g., patient monitor 102 using public key cryptography. In public key cryptography, the device 134 has a public key, a private key, and a digital certificate. The monitor 102 and/or central station 128 may also include a public key, private key and digital certificate if mutual authentication is implemented between the device 134 and monitor 102 (or central station 128). The private key is used by the device 134 to generate an encrypted message Private key [RAND, Device ID, User ID]. The device 134 sends the encrypted message, IDs, and its certificate to the monitor 102. The monitor 102 may check the certificate to verify that the it is legitimate or send it to the central station to verify the certificate. Once the certificate is verified, the monitor 102 will be assured that the public key of the device 134 in the certificate is valid. Then, the monitor 102 uses the public key to decrypt (reverse the encryption) of the encrypted message sent by the device 134. Once decrypted, the monitor 102 compares the decrypted device ID (or another value) with the unencrypted version. If they match, the monitor 102 can authorize access to patient data to the device 134. The device 134 and/or monitor 102 may generate a secret key or random value (e.g. RAND) that may be uses for establishing an encrypted session. Again, the authorization/authentication functions of the monitor 102 may be performed by the central station 128 instead or performed solely by the monitor 102. Once the device and/or user is authorized access, an encrypted session and/or channel may be established between the device 134 and monitor 102 (and/or central station 128) to protect data transmissions to and from the device 134.

It will be apparent to those of ordinary skill in the art that certain aspects involved in the operation of the device 134, monitor 102, and/or central station 128 may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, or flash memory device having a computer readable program code stored thereon.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

The invention claimed is:
1. A patient monitoring system comprising:
a patient monitoring device for monitoring a physical condition of a patient, the patient monitoring device including:
a first data interface for receiving physiological data from a patient sensor,
a second data interface for sending patient data to a patient monitoring network via a first communication channel and for receiving, from a central station, authorization information for authorizing an access request to the patient data by a portable communications device, and
a third data interface for receiving the access request to the patient data from the portable communications device via a second communication channel, wherein the access request includes an access code,
the central station being located remotely from the patient monitoring device and in communication with the patient monitoring network, the central station storing access control data associated with the patient monitoring device for authorizing the access request to the patient data by the portable communications device,
the portable communications device including:
a user interface for displaying a patient physical condition based on patient data received from the patient monitoring device,
a first communication interface for sending the access request to the patient monitoring device via the second communication channel, wherein the first communication interface is configured to communicate when within a close proximity of the patient monitoring device using a personal area network, a second communication interface for receiving the patient data, wherein the second communication interface is configured to communicate using a wide area network and a processor for generating the access request, wherein the first communication channel is different than the second communication channel, and wherein a range of the second communication interface exceeds a range of the first communication interface.

2. The system of claim 1, wherein the access code is derived from a secret.

3. The system of claim 2, wherein the access code includes a cryptographic response to a challenge.

4. The system of claim 2, wherein the secret includes an ephemeral secret.

5. The system of claim 1, wherein the patient monitoring device grants access to the patent data based on whether the access code is acceptable.

6. The system of claim 5, wherein the access code is determined to be acceptable by comparing the access code with a stored access code.

7. The system of claim 1, wherein the first communication channel includes a first wireless channel.

8. The system of claim 7, wherein the first wireless channel is limited in range.

9. The system of claim 8, wherein the portable communications device is in relatively close proximity to the patient monitoring device.

10. The system of claim 1, wherein the portable communications device includes a handheld device.

11. The patient monitoring device of claim 1, wherein the authorization information includes an authorization code.

* * * * *